(12) United States Patent
Pahlavan et al.

(10) Patent No.: US 10,175,205 B2
(45) Date of Patent: Jan. 8, 2019

(54) SYSTEM AND METHOD FOR CRACK MONITORING

(71) Applicant: Nederlandse Organisatie voor toegepast-natuurwetenschappelijk onderzoek TNO, 's-Gravenhage (NL)

(72) Inventors: Lotfollah Pahlavan, 's-Gravenhage (NL); Arno Willem Frederik Volker, 's-Gravenhage (NL)

(73) Assignee: NEDERLANDSE ORGANISATIE VOOR TOEGEPAST- NATUURWETENSCHAPPELIJK ONDERZOEK TNO, 'S-Gravenhage (NL)

( * ) Notice: Subject to any disclaimer, the term of this patent is extended or adjusted under 35 U.S.C. 154(b) by 172 days.

(21) Appl. No.: 15/115,826

(22) PCT Filed: Feb. 4, 2015

(86) PCT No.: PCT/NL2015/050075
§ 371 (c)(1),
(2) Date: Aug. 1, 2016

(87) PCT Pub. No.: WO2015/119498
PCT Pub. Date: Aug. 13, 2015

(65) Prior Publication Data
US 2017/0074832 A1 Mar. 16, 2017

(30) Foreign Application Priority Data

Feb. 5, 2014 (EP) .................................... 14153948
May 13, 2014 (EP) .................................... 14168054

(51) Int. Cl.
*G01N 29/44* (2006.01)
*G01N 29/14* (2006.01)

(52) U.S. Cl.
CPC .......... *G01N 29/14* (2013.01); *G01N 29/4472* (2013.01); *G01N 2291/0289* (2013.01); *G01N 2291/0427* (2013.01)

(58) Field of Classification Search
CPC ............... G01N 29/14; G01N 29/4472; G01N 2291/0289; G01N 2291/0427
(Continued)

(56) References Cited

U.S. PATENT DOCUMENTS 3,713,127 A  1/1973  Keledy et al.
4,435,984 A  3/1984  Gruber
(Continued)

FOREIGN PATENT DOCUMENTS

WO  WO0150122 A1  7/2001
WO  WO03106958 A2  12/2003
(Continued)

OTHER PUBLICATIONS

Keshtgar et al., "Acoustic Emission-Based Fatigue Crack Growth Prediction," Reliability and Maintainability Symposium (RAMS), 2013 Proceedings—Annual, IEEE, Jan. 28, 2013.
(Continued)

*Primary Examiner* — J M Saint Surin
(74) *Attorney, Agent, or Firm* — Hoffmann & Baron, LLP

(57) ABSTRACT

In accordance with an aspect of the present application, a system is provided for crack monitoring in a structure of interest, comprising means for extracting wave modes existing in a frequency interval of interest, means for finding a source of emission on the structure of interest, means for correcting for dispersion to reconstruct an original ratio of wave modes at the source of emission, and means for correlating the original ratio of wave modes to a crack depth. One advantage of this solution in contrast to prior art techniques is that no a priori knowledge on propagation
(Continued)

speed is necessary since actual wave modes can be detected from dispersion relations of wave modes, e.g. Lamb waves at a fixed frequency band in accordance with their calculated speeds. Decentralized acquisition and processing, i.e. monitoring a structure from a localized area, is an important feature of this solution, consequent to which, the data transfer and storage are reduced substantially.

8 Claims, 11 Drawing Sheets

(58) Field of Classification Search
USPC .......................................................... 73/587
See application file for complete search history.

(56) References Cited

U.S. PATENT DOCUMENTS

| | | | | |
|---|---|---|---|---|
| 5,014,556 | A * | 5/1991 | Dunegan | ............ B06B 3/00 73/1.86 |
| 5,635,643 | A | 6/1997 | Maji | |
| 5,714,687 | A * | 2/1998 | Dunegan | ............ G01H 1/00 73/587 |
| 5,734,588 | A | 3/1998 | Rose et al. | |
| 5,929,315 | A | 7/1999 | Dunegan | |
| 6,173,613 | B1 * | 1/2001 | Dunegan | ............ G01H 1/00 73/1.82 |
| 6,751,560 | B1 | 6/2004 | Tingley et al. | |
| 2002/0139194 | A1 | 10/2002 | Mars | |
| 2003/0009300 | A1 | 1/2003 | Giurgiutiu | |
| 2003/0167141 | A1 | 9/2003 | Staszewski | |
| 2007/0150213 | A1 | 6/2007 | Kim et al. | |
| 2009/0048789 | A1 | 2/2009 | Yu et al. | |
| 2009/0070048 | A1 * | 3/2009 | Stothers | ............ G01N 29/045 702/39 |
| 2009/0139337 | A1 | 6/2009 | Owens et al. | |
| 2009/0150094 | A1 | 6/2009 | Van Velsor et al. | |
| 2010/0042338 | A1 | 2/2010 | Giurgiutiu et al. | |
| 2010/0217544 | A1 | 8/2010 | Yan et al. | |
| 2010/0312493 | A1 | 12/2010 | Purekar et al. | |
| 2011/0041612 | A1 | 2/2011 | Paige | |
| 2012/0209538 | A1 | 8/2012 | Caicedo et al. | |
| 2013/0118261 | A1 * | 5/2013 | Stothers | ............ G01M 5/0033 73/645 |
| 2013/0132002 | A1 | 5/2013 | Falsetti et al. | |

FOREIGN PATENT DOCUMENTS

| | | |
|---|---|---|
| WO | WO12066398 A1 | 5/2012 |
| WO | WO12172124 A1 | 12/2012 |

OTHER PUBLICATIONS

Tian et al., "Near-field beamforming analysis for acoustic emission source localization," Ultrasonics 52 (2012) 587-592.

Sicard et al., "A numerical dispersion compensation technique for time recompression of Lamb wave signals," Ultrasonics 40 (2002) 727-732.

Lamb, "On Waves in an Elastic Plate," Proc. Roy. Soc. London, Ser. A 93 (1917), 114-128.

McLaskey et al., "Beamforming array techniques for acoustic emission monitoring of large concrete structures," Journal of Sound and Vibration 329 (2010) 2384-2394.

* cited by examiner $$\Delta t_{ij} = \arg\max_{\tau \in \mathbb{R}} \left\| \int \hat{S}_j(t) \hat{S}_i(t+\tau) dt \right\|_{\infty} \quad (1)$$

$$\arg\min_{x,y,c_g} F(x_c, y_c, c_g, \Delta t_{ij}), \ \forall i,j \in [1,2,\ldots,n], \ \text{subject to:} \ (x,y) \in \Omega \ \text{and} \ c_g \in [c_{g0}(\omega), c_{A0}(\omega)] \quad (2)$$

$$F(x_c, y_c, c_g, \Delta t_{ij}) = \sum_{j=1}^{n} \left[ \Delta t_{ij} - \frac{1}{c_g} \left[ \sqrt{(x_i - x_c)^2 + (y_i - y_c)^2} - \sqrt{(x_j - x_c)^2 + (y_j - y_c)^2} \right] \right]^2, \ \forall i,j \in [1,2,\ldots,n] \quad (3)$$

$$\nabla \cdot \sigma + \mathbf{f} = \rho \ddot{u}, \ \text{in} \ \Omega \in \mathbb{R}^3, \quad (4)$$

$$\sigma(x_c, y_c, z_c) = \sigma_{AE}, \quad (5)$$

FIG. 4C

SYSTEM AND METHOD FOR CRACK MONITORING

This application is the U.S. National Phase of, and Applicants claim priority from, International Patent Application Number PCT/NL2015/050075 filed Feb. 4, 2015, which claims priority from EP 14153948.6 filed Feb. 5, 2014 and EP 14168054.6 filed May 13, 2014, each of which is incorporated herein by reference.

FIELD OF THE INVENTION

The present invention relates to a system and method for crack monitoring, as well as to a computer program for this method.

BACKGROUND OF THE INVENTION

Early-stage detection of cracks in large civil, offshore, and aerospace structures is of a crucial importance for (i) estimation of the remaining service life, and (ii) assuring safety of these structures. Cracks are not limited to, but mainly due to fatigue loading, e.g. traffic load on a bridge. The structures/structural components of interest for monitoring are made of thin-walled components i.e. a structure having a thickness which is significantly smaller than its other two dimensions. For such structures, acoustic emission (AE) is one of the most widely-used crack monitoring techniques consequent to (i) having a relatively large coverage area, (ii) being sensitive to small cracks, even at the initiation phase, and (iii) reasonably low implantation costs. Acoustic emission systems work based on the fact that the activity of structural defects release acoustic energy signals propagating inside and on the surface of the structure as guided wave (GW) modes in thin-walled structures, mainly the fundamental symmetric Lamb wave S0 and the fundamental antisymmetric lamb wave A0. Typically, the S0 waves travel at a higher speed than the A0 waves. To find the location of an AE source, e.g. an active crack, in the conventional triangulation-based AE approach, synchronized measurements from at least tree sensor locations are required. The typical frequency range of AE signals is [10 kHz-1 MHz], demanding sampling rates up to a few mega-samples per second. It is believed that three main issues have hindered the growth rate of AE techniques for monitoring large scale structures, as listed below.
1. Required sensor network. The main challenges include the communication, synchronization, and connection of a large number of sensors to a central processing unit.
2. Storage, aggregation, and forwarding of enormous amount of data, being recorded at the mentioned sampling rates for duration of the monitoring, e.g. a few months.
3. Complexity of AE signals and substantial uncertainty in their interpretation coming from (i) multimode nature of guided waves (GW) in thin-walled structures, (ii) dispersion of guided waves, (iii) geometrical spreading, (iv) different attenuation behavior for different GW modes, (v) environmental noise, and (vi) reflection and refraction of GW due to interaction with structural entities, e.g. stiffeners.

In addition to these difficulties, yet existing AE methods do not provide reliable quantitative information about the cracks, e.g. length and depth. In U.S. Pat. No. 5,929,315 an AE method and apparatus is disclosed for detecting and measuring cracks in plate-like structures. A false aperture transducer is designed to provide a criterion for filtering out extraneous noise in AE signals by computing the ratio of the high-frequency peak amplitude to low-frequency peak amplitude. A calibration curve correlating crack depth to the amplitude ratio was obtained by (i) simulating crack growth in a fracture specimen coupled to a test structure or field structure, and (ii) measuring acoustic emission signal in the structure by the false aperture transducer. The calibration curve correlates simulated crack depth percentage with computed peak amplitude ratio of the measured signal. Location of a crack-like source can be determined by detecting the AE signal from three different locations and ascertaining the point of intersection.

In the referenced disclosure, wave modes are separated in accordance with frequency filtering, i.e. a high-pass (>100 kHz) and band-pass (20-80 kHz) frequency filter for in-plane and out-of-plane waves. The disclosure relies on non-dispersive propagation of 'flexural wave modes' which have differing ratios for out of plane and in-plane motions. However, the method proposed suffers from practical limitations since multiple wave modes can exist in the entire frequency-band (>20 kHz), and the amplitudes in the above-mentioned ranges are not generally representative for the assumed wave mode. It is not physically realistic that the wave modes propagate at predetermined speeds in a non-dispersive manner. The invention has therefore as an object to improve the reliability of crack detection and growth monitoring, that the prior art fails to resolve. In addition, through its novel formulation, the three issues listed earlier on the application of AE for large-scale structures may be overcome, i.e. the complex sensor network, large amount of data for storage and forwarding, complexities of guided wave signals.

SUMMARY OF THE INVENTION

In accordance with an aspect of the present application, a method and corresponding system is provided for evaluating crack monitoring in a structure of interest using AE sensing, comprising:
  placing a plurality of AE detectors on the structure of interest, having relative known positions;
  detecting time traces of an AE source in the selected detectors;
  detecting relative time differences in the time traces;
  based on the detected time differences: finding a source of emission on the structure of interest and extracting a dominant wave mode existing in a frequency interval of interest by minimizing an error function, from a model of the structure of interest;
  identifying, in the frequency interval of interest; the non-dominant wave mode in a time window of interest;
  correlating the ratio of wave modes to a crack depth location using a finite element analysis for rendering a characteristic curve;
  populating a history bank crack depth ratios measured for corresponding locations, so that for a selected crack, identified by a calculated location of the AE source, its deepness be resolved by matching a calculated ratio with a progress in time of the specific ratio position in progress on the characteristic curve.

One advantage of this solution in contrast to prior art techniques is that no a priori knowledge on propagation speed is necessary since actual dominant wave modes can be detected from dispersion relations of wave modes in accordance with the group speed identified in the error-minimization problem, e.g. Lamb waves at a fixed frequency band in accordance with their calculated group speeds. It is remarked that the term 'dominant wave mode' refers to a wave mode carrying more acoustic energy than a 'non-dominant wave mode' as is well known from guided wave theory.

Accordingly a decentralized and quantitative AE system is provided based on combining a beamforming AE technique and guided wave theory. A distinguishing aspect of the introduced beamforming analysis from conventional analysis is the unknown speed of the waves in its formulation. In an embodiment decentralized crack localization is provided with a compact group of sensors, e.g. 4, that can cover an area of 3-300 m2, and crack size is estimated by analysis of the proportion of the guided wave modes released by the crack for large metallic structure, e.g. road constructions, building structures, pressure vessels, and pipelines.

FIGURES

DETAILED DESCRIPTION

Figure 1A:
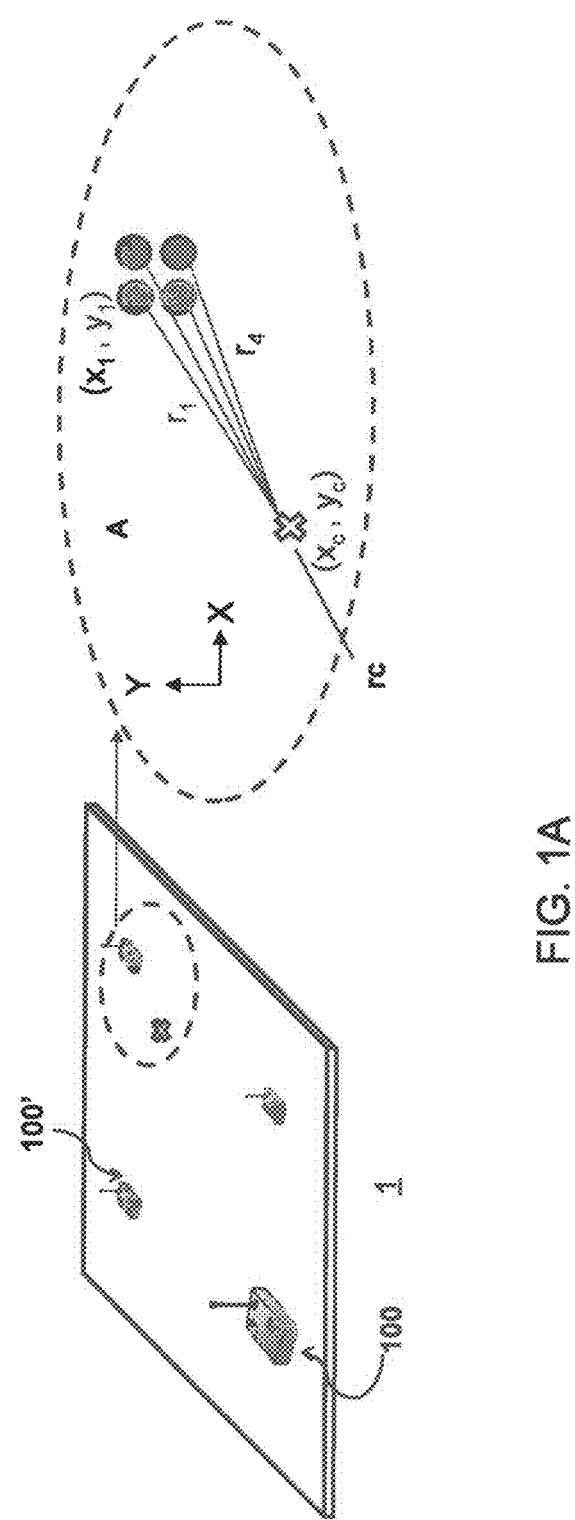
FIG. 1 shows a schematic arrangement of a setup in accordance with an embodiment of the invention.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

Throughout the application, any means for carrying out the disclosed methods, in particular, as further clarified below: means for extracting wave modes existing in a frequency interval of interest, means for finding a source of emission on a structure of interest, means for correcting for dispersion along the detection path to reconstruct an original signal at the source of emission, and means for correlating the original ratio of wave modes to a crack depth can be implemented in hardware and/or software and as structurally identifiable by the function it perform in the system; i.e. the function is physically implemented in hardware and/or software or information structures transmitted through the network. The identified functions may be implemented in hardware or software, to provide dedicated processing circuitry that processes input data read from system resources. A server function may e.g. be provided by a connected physical network device, but may also be formed as a virtual device, functioning in a network, and which may be implemented on a hardware resource that can be reached via network communication. These functions may be executed by one or more processors configured to perform operational acts in accordance with the present systems and methods, such as to provide control signals to the various other module components. The processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Any type of processor may be used such as dedicated or shared one. The processor may include micro-controllers, central processing units (CPUs), digital signal processor s (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the size and relative sizes of systems, components, layers, and regions may be exaggerated for clarity. Embodiments are described with reference to schematic illustrations of possibly idealized and/or intermediate structures of the invention.

Figure 1B:
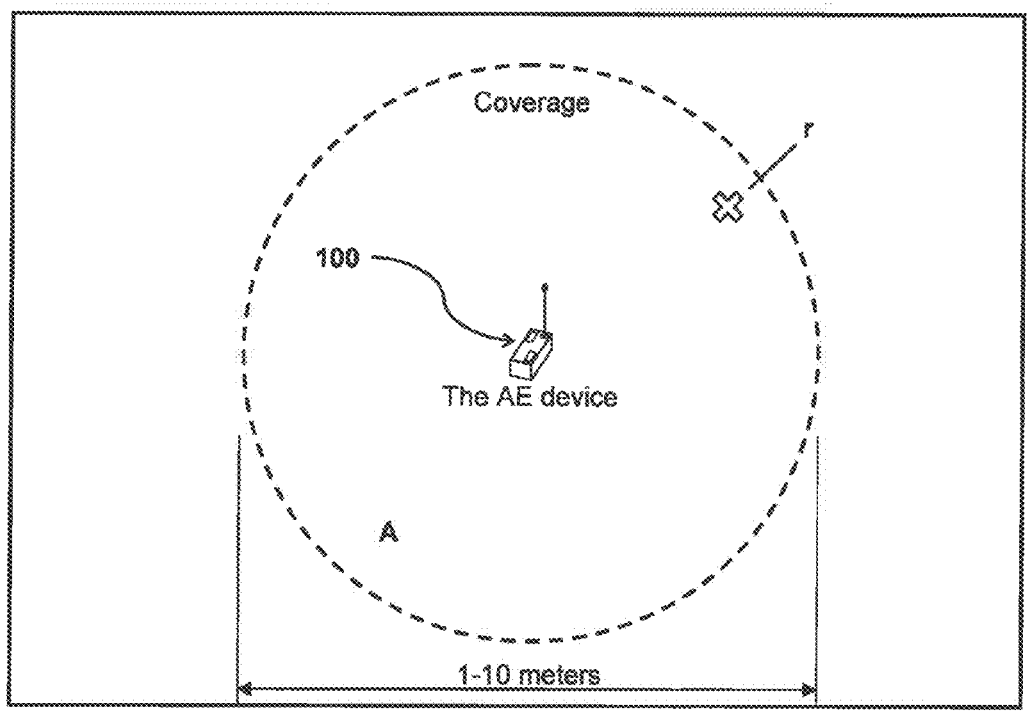

In FIG. 1A a schematic arrangement of a setup in accordance with an embodiment of the invention is shown. To monitor a large-scale structure, a cluster of AE systems may be used as shown in FIG. 1A. Every AE node 100, 100' can work independently with a circular coverage area 3-300 m2, as shown in FIG. 1A (right). Consequently, the AE device 100 does not need to communicate with sensors at other nodes 100' (if they exist) which is of a great importance in practical situations, e.g. bridges. FIG. 1B in more detail shows cover area A, wherein an AE device 100, centrally located in detection area A on a thin-walled plate object 1, e.g. a bridge deck plate.

Figure 1C:
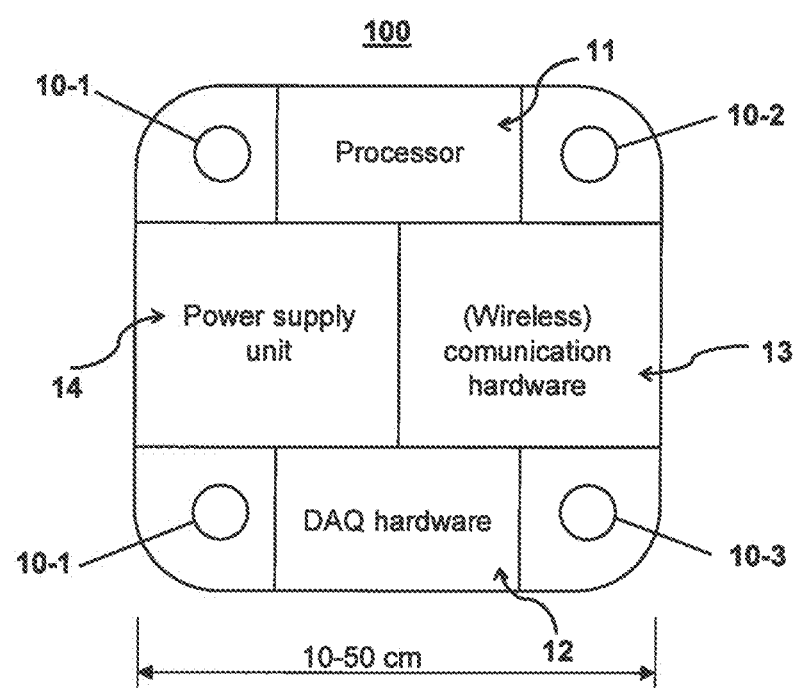

As shown in FIG. 1C, stand-alone compact AE device 100 is provided to monitor the activity, location (xc, yc), size, and growth of cracks rc, in cover areas A of thin-walled structures 1. The device comprises a number of individual AE sensors 10-1 . . . 10-4, for example 4. In addition the device comprises of a processor 11, a data acquisition unit 12, communication hardware 13 for data transfer, and power supply 14. In a preferred embodiment, the communication hardware 13 is provided with wireless communication capability. Advantageously sensors 10-1 . . . 10-4 are placed relatively close to each other, e.g. in a range of 5-50 cm, to minimize a variation of (i) signal dispersion, (ii) geometrical spreading, (iii) direction dependent propagation properties, (iv) attenuation, and (v) influence of interaction with structural entities, between the collected signals. In addition to the features regarding the reduced complexities of GW mode detection, the following merits of the proposed approach are notable:

1. processing and source localization is completely decentralized,
2. inter-communication between the nodes is not needed,
3. monitoring system can become intrinsically on-line,
4. hardware and installation costs can be substantially reduced,
5. lower SNR values can be dealt with since the signals at each node are correlated, hence the inspection range is extended. By correlating the gathered responses in sensors 10-1 . . . 10-4, the difference in the arrival times of the AE signals at different locations can be accurately obtained in this settings. These detector locations are for example placed in a range of 0.1-10 m away from a potential crack location. An important aspect is that wave mode composition ratio of S0/A0 is also a function of distance from the source and frequency for which the dispersion correction is carried out.

Figure 2:
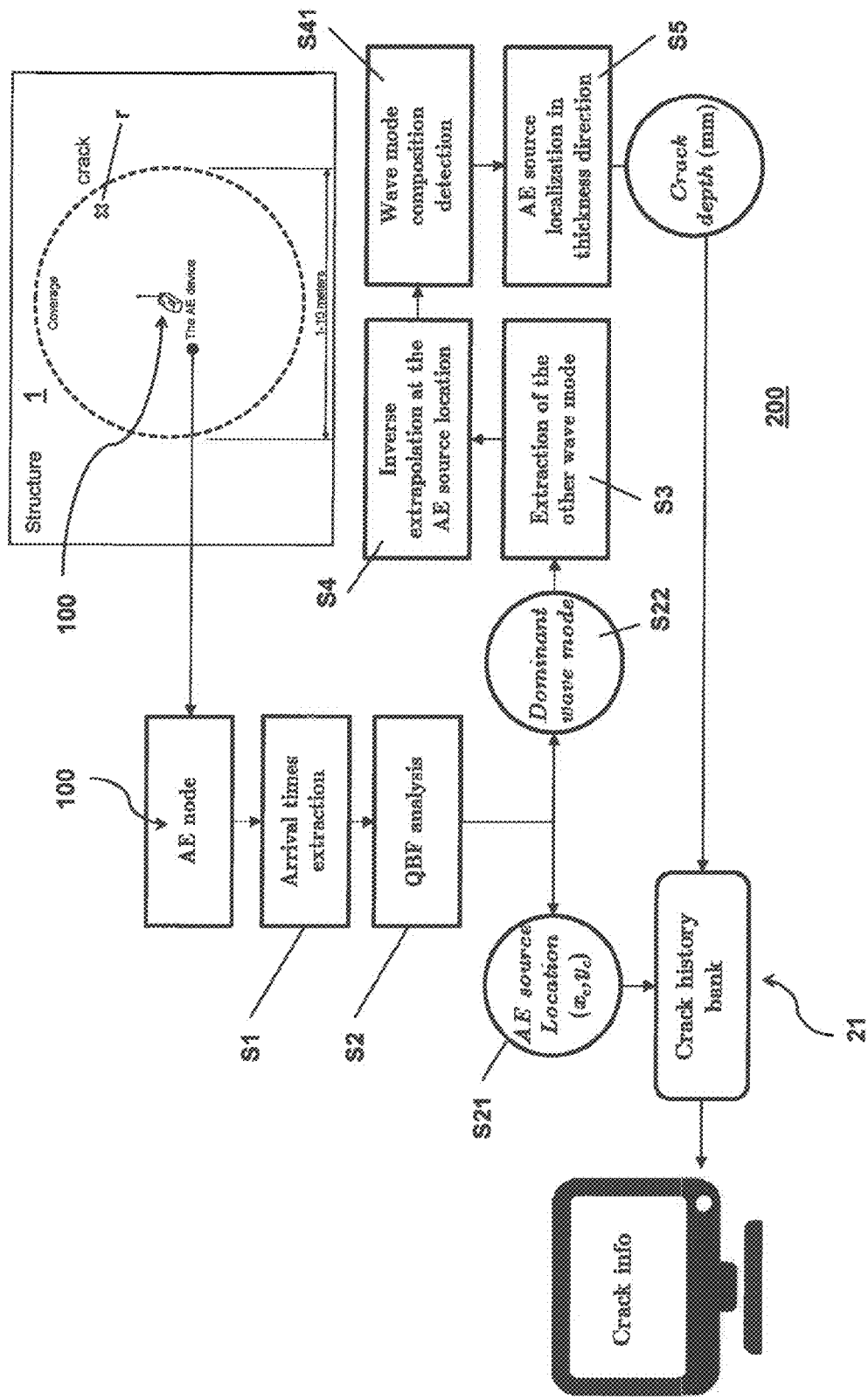
FIG. 2 shows a detailed operation/analysis flowchart of an AE system according to an aspect of the invention.

FIG. 2 shows in more detail a schematic flow chart of a data collection and processing system 200 wherein node may be incorporated 100, or may be communicatively coupled, for example, to a central data processing system 200, that may be wirelessly connected or connected via a physical network to a plurality of nodes.

An important feature of the system is a history bank of crack growth, which is used to benefit, as will be described herebelow, to analyze the sensor responses of the various nodes further discussed below.

In addition system 200 has processing circuitry to receive node data 100 that is substantially reduced (orders of magnitude) since, in this embodiment, (only) the result of the processed data from a node 100 comprising plurality of sensors 10-1 . . . 10-4 may be stored and transferred, instead of unprocessed data from each sensor. The computer implemented method executed by hardware run on this system is as follows. In a first step s1, the node 100 arrival times of an impinging wave is detected by sensors 10-1 . . . 10-4, as further illustrated in FIG. 1*c*. In a second step s2, next, a specific beamforming analysis based on the guided waves characteristics is executed. An example of conventional beamforming for a plate structure using guided wave modes is described in "Near-field beamforming analysis for acoustic emission source localization", Tian He et al, Ultrasonics 52 (2012) 587-592. In the present application, the arrival times obtained from the AE signals are used for localization of the AE source, wherein in contrast to conventional beam forming, the speed of the waves is also unknown. For every set of waveforms recorded at the sensor locations, the most plausible wave mode (and speed) is identified in an optimization routine in accordance with the dispersion curves for the structural component under investigation, as will be described in more theoretical detail with reference to FIG. 3*b*. For the sake of brevity, this formulation will also be referred to as quasi-beamforming (QBF) in the reminder of this document.

Outputs of S2 are the identification of a dominant wave mode S22 and the finding S21 of a source of emission on a structure of interest 1, i.e. the AE source location of a detected crack r (xc, yc) by defining an error-minimization problem.

In a next step S3, based on the identified dominant wave mode of S21, other wave modes are extracted in the same frequency interval, further exemplified in FIG. 4. In a further step S4, a correction is carried out for dispersion of guided waves to reconstruct (step S41) an original ratio of wave modes at the source of emission. In other words, the original waveforms at the AE source are retrieved using a dispersion correction routine, which compensates for variation of the signal shape over the propagation distance, in this case from the crack location to the AE sensors. An example for dispersion correction of guided waves can be found in Sicard et. Al. (2002). Note that the differential arrival times can be extracted from the dispersion corrected signals at this stage and replace the original values obtained from correlation of non-dispersion corrected signals. The updated differential arrival times can be used for improved location detection of the crack.

Finally the output of step S41, i.e. an original ratio of wave modes originating from crack location r is correlated in a step S5 to a crack depth using a model, further exemplified in FIG. 5.

Figure 3A:
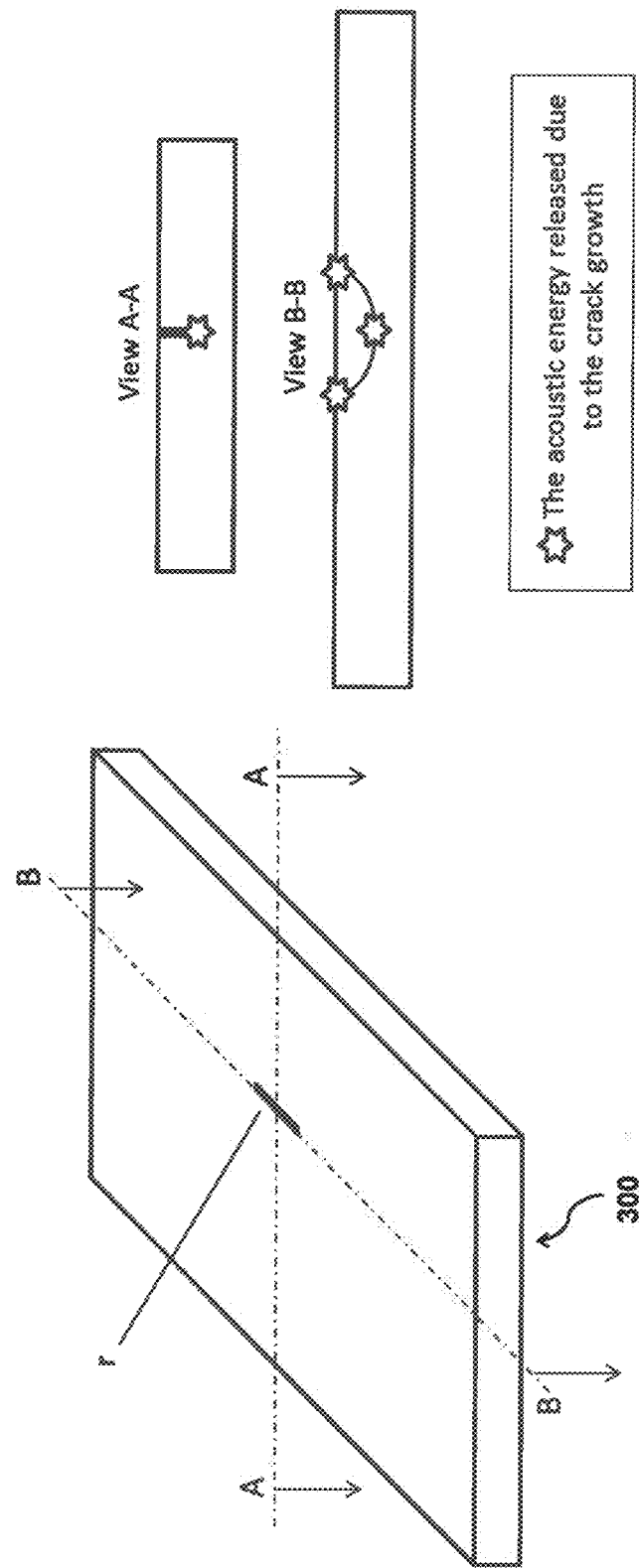
FIG. 3 shows a schematic illustration of acoustic energy release due to crack growth and corresponding wave mode propagation.

FIG. 3 shows a theoretical context of the detection of acoustic energy released due to crack growth. Growth of fatigue cracks in metals is associated with release of acoustic energy due to the breakage of the internal structure of the material being under excessive stress. The source and mechanism of this release of energy for a crack of certain depth and size are shown schematically in FIG. 3A, with views A-A and B-B in cross and longitudinal direction of a crack r extending along direction B-B in a plate structure 300. The source of each AE signal is, in essence, a point on the leading edge of the crack, which can be used for depth estimation. As mentioned hereabove, the proposed AE solution extracts the information about the location of these sources in the plane of the thin-walled structure explicitly using a quasi-beamforming scheme, whereas the information about the AE source in the thickness-wise direction are obtained implicitly from the guided wave decomposition analysis. This analysis is based on the fact that the composition of the received signal in terms of S0 and A0 waves is a function of the source location in the thickness direction by dispersion effects.

Therefore, in the guided wave analysis dispersion curves of phase speed and group speed for a medium are calculated to describe properties of the waves traveling within that medium. Phase speed and group speed dispersion curves respectively correlate the speed of each individual phase and an envelope of a wave mode to frequency. For a thin-walled flat structure extended, waves polarized in the vertical plane are described with the following transcendental equations [Lamb, H. On Waves in an Elastic Plate. Proc. Roy. Soc. London, Ser. A 93, 114-128, 1917]:

$$\frac{\tan(\beta d/2)}{\tan(\alpha d/2)} = \frac{4\alpha\beta k^2}{(k^2-\beta^2)^2} \text{ and } \frac{\tan(\beta d/2)}{\tan(\alpha d/2)} = -\frac{(k^2-\beta^2)^2}{4\alpha\beta k^2} \quad (1)$$

with

-continued $$\alpha^2 = \frac{\omega^2}{c_l^2} - k^2 \text{ and } \beta^2 = \frac{\omega^2}{c_t^2} - k^2 \qquad (2)$$

In the equations above, ω is angular frequency, k is the wave number, d is the thickness of the plate, and $c_l$ and $c_t$ denote the longitudinal and shear wave speeds, respectively. Once the wave number-angular frequency is obtained, the phase speed $c_p$ and group speed $c_g$ can be calculated as:

$$c_p = \omega/k \text{ and } c_g = d\omega/dk \qquad (3)$$

Figure 3B:
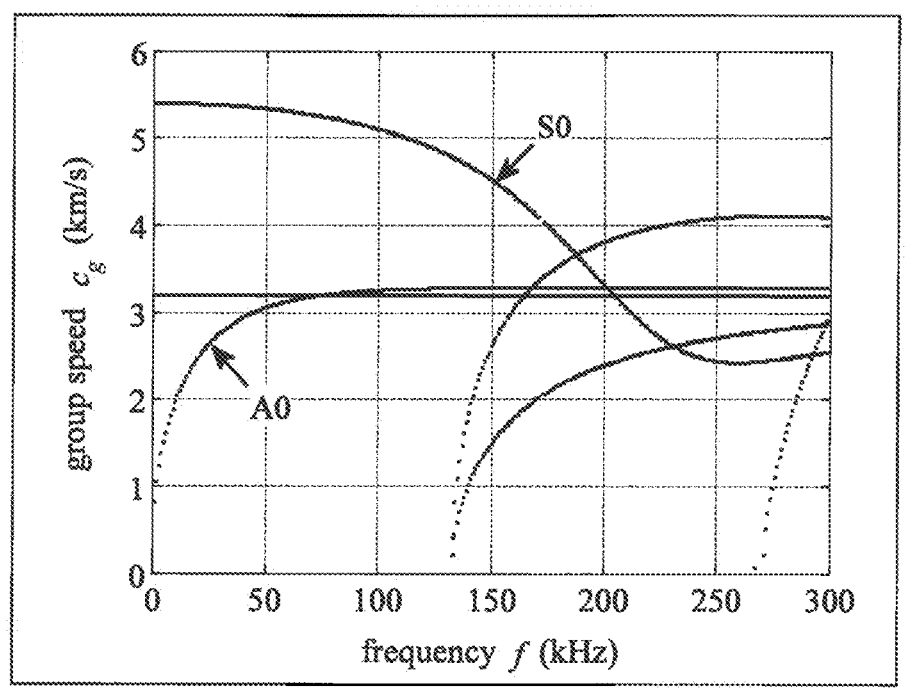

The dispersion curves for the fundamental modes S0 and A0 can be readily extracted from the equations above. An example of the group speed dispersion curve for construction steel can be seen in FIG. 3B showing an graph illustrating group speeds for specified wave modes S0 and A0 in a steel plate of 12 mm thick. The group speed of the S0 wave, in a relevant frequency domain of for example 100-250 kHz is higher in the 150-200 kHz area typically 4-5 km/s and lower in the area above 200 kHz, where the A0 wave mode is typically around 3 km/s. For a given structure of a material with known thickness, dispersion curves can be obtained from the guided (Lamb) wave theory, as discussed earlier. A generalized formulation can be used to obtain the dispersion curves for non-flat structures, e.g. storage tanks and pipes.

Figure 4A:
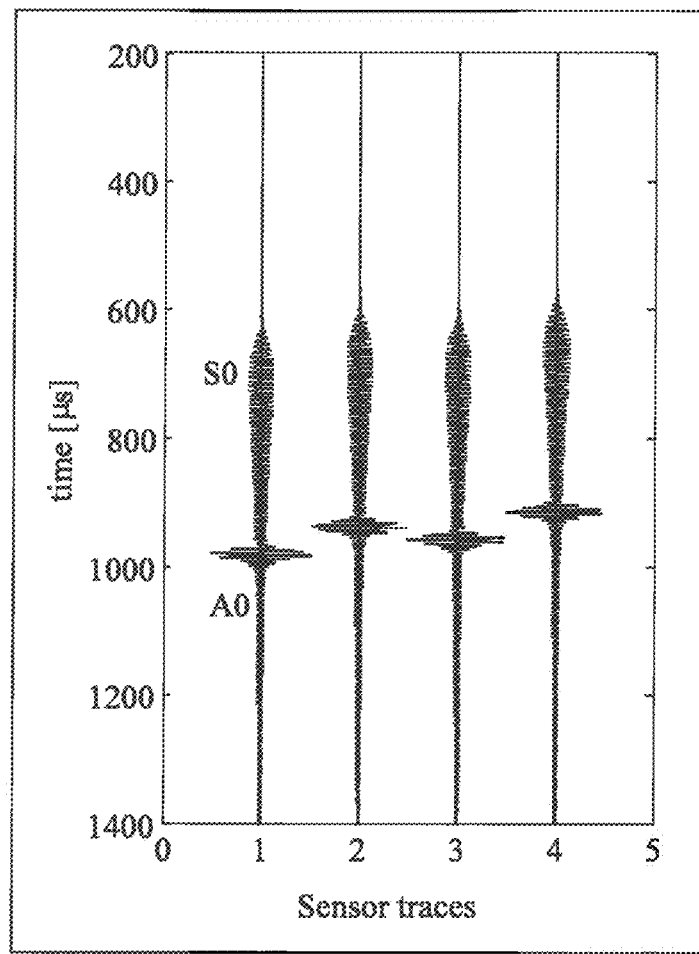
FIG. 4 shows sample AE waveforms and frequency decomposition detected in an experiment.

FIG. 4 shows a practical illustration how the wave mode analysis is carried out in sample waveforms obtained from experiments with the plate structure 300. In FIG. 4A traces 1-4 are shown, collected by corresponding AE sensors 10-1.4, e.g. upon crossing a predefined threshold criterion. In the first trace, an arrival of the faster S0 wave can be discerned about 600 ms, and later the slower A0 wave about 1000 ms, and time shifted and dispersed equivalents are detected in the other traces 2-4.

Figure 4B:
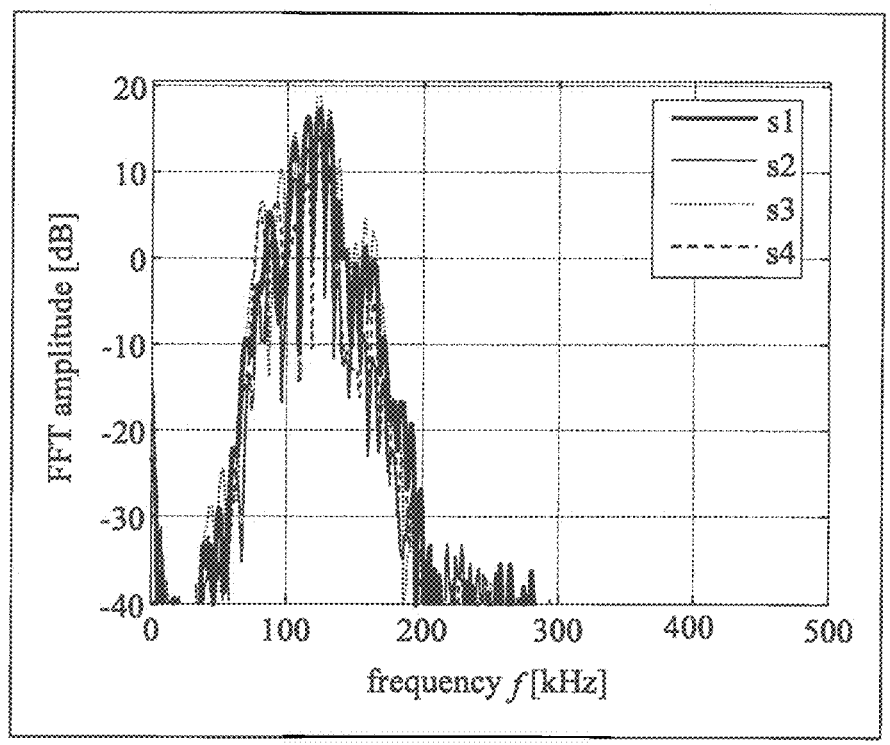

From a time window of interest thus obtained, relative arrival times are extracted by means of cross-correlation operation subsequent to band-pass filtering of the row signals. If the signal recorded at sensor location j is denoted by Sj, the differential arrival time can be calculated (see FIG. 4C1) as:

$$\Delta t_{ij} = \operatorname*{argmax}_{\tau \in R} \left\| \int \hat{S}_j(t) \hat{S}_i(t+\tau) dt \right\|_\infty \qquad (1)$$

where $\|\cdot\|_\infty$ and the 'hat' sign indicate the maximum norm, and the band-pass filtering, respectively. Band pass filtering in the example is performed in a range 100-250 kHz, blocking frequencies outside the range, for signals having frequency decompositions shown in FIG. 4B showing maximum amplitudes for about 150 kHz (full width half maximum about 80 kHz). Next in accordance with step S2 discussed in FIG. 2, quasi-beamforming is carried out to identify as output a dominant wave S21 mode and calculated AE source location S22. This is achieved in accordance with the minimization problem mentioned earlier (FIG. 4C2):

$$\operatorname*{argmax}_{x_c, y_c, c_g} F(x_c, y_c, c_g, \Delta t_g), \forall\, i, j \in [1, 2, \ldots, n], \qquad (2)$$

subject to: $(x, y) \in \Omega$ and $c_g \in [c_{S0}(\omega), c_{A0}(\omega)]$ where xc and yc denote the coordinates of an AE source in a plane of geometry (see for example, FIG. 1 left), cg is the speed of the dominant wave mode, Ω (Omega) is the physical domain under inspection in the plane of geometry, cS0 and cA0 are the group speeds of the fundamental guided wave modes S0 and A0 as functions of angular frequency ω (omega) in the frequency band of interest, see for example FIG. 4b, and F is the generic functional form of the error function associated with the assumed combination of the source location, speed of the dominant wave mode, and the identified arrival times from Equation (1). An example is a minimum quadratic function or other type of error function (e.g. exponential) that can be optimized, for example F can be (See FIG. 4C3):

$$F(x_c, y_c, c_g, \Delta t_g) = \sum_{j=1}^{n} \left( \Delta t_{ij} - \frac{1}{c_g} \left[ \frac{\sqrt{(x_i - x_c)^2 + (y_i - y_c)^2}}{\sqrt{(x_j - x_c)^2 + (y_j - y_c)^2}} \right] \right)^2, \qquad (3)$$

$$\forall\, i \in [1, 2, \ldots n]$$

In the set of traces in this way, a dominant wave mode and corresponding speed is detected. Based on the identified dominant wave mode, which can be the faster S0 wave or the slower A0 wave, the other mode is also detected in the calculated time window corresponding to step S3 previously discussed in FIG. 2.

The temporal position of this window is chosen equal to the distance of the AE sensors to the calculated crack location (xc, yc) divided by the group speed of the non-dominant wave mode given by the dispersion curve at the frequency of interest, measured from the time of the AE event, i.e. the distance from the AE sensors divided by the group speed of the dominant wave mode.

The length of this window can be tuned from a few dozen microseconds to a few hundred microseconds, depending on the geometry and configuration. Having calculated the composition of the S0 and A0 waves at the identified AE source location while taking into account dispersion correction, an updated crack location can be estimated by further minimizing Equation (2) using the corrected arrival times corresponding to step S4 previously discussed in FIG. 2.

Furthermore having the actual wave modes compositions thus identified, a crack depth of the acoustic source origin can be calculated in an estimation using a characteristic curve correlating the crack depth to the ratio of S0 to A0 waves. The characteristic curve can be obtained from a forward analysis to express S0-to-A0 ratio as a function of the AE source depth (see FIG. 3C). The analysis can be analytical, e.g. from Rayleigh-Lamb equations, or numerical, e.g. from finite element or finite difference analysis. With such methods, the following wave equation governing the wave motion in linear elastic materials is solved:

$$\nabla \cdot \sigma + f = \rho \ddot{u}, \text{ in } \Omega \in \mathbb{R}^3, \qquad (4)$$

The solution is subject to appropriate boundary conditions at the crack location. In the equation above, σ (sigma), f, σ (rho), u and Ω (Omega) denote the 3×3 stress tensor, external force vector, material density, displacement vector, and the physical domain of the structure respectively. An appropriate stress boundary can be a prescribed stress function at the assumed emission point of the crack (xc, yc, zc) i.e.

$$\sigma(x_c, y_c, z_c) = \sigma_{AE}, \qquad (5)$$

where zc is the emission depth. Selection of the frequency content of such a function, i.e. $\sigma_{AE}$ (sigma AE), is under the constraint that it should exist in the frequency band of the AE sensors and the possible band pass filter applied.

Figure 5A:
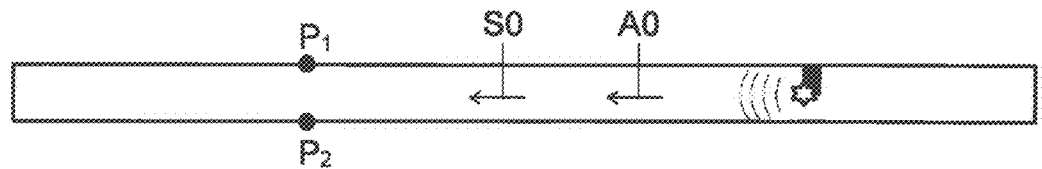
FIG. 5 shows an exemplary chart for Lamb wave mode analysis due to the acoustic emission at the crack at corresponding depths.

FIG. 5A shows schematically that depending on crack depth, a specific composition of A0 and S0 wave modes is released, which can be measured by measurement positions P1, P2. A correlation curve (see FIG. 5B) can for example be extracted using finite element analysis, known to the skilled person for a given structure. The structure that is shown is a flat plate, where boundary conditions apply as discussed in relation to FIG. 3 and known to the skilled person. In this way, a footprint of the crack edges can be traced back and identified by the monitoring system during the crack growth process. The analysis distinguishes points P1 and P2 on opposite positions of the modeled structure, to identify the symmetric waves (S0, . . . ) from anti-symmetric (A0, . . . ) ones and determine their ratio. In the alternative, different points P1 and P2 may be used, for example on a single face of the structure. Similar analysis can be performed for curved structures if the curvature is considered in the FEM model.

Figure 5B:
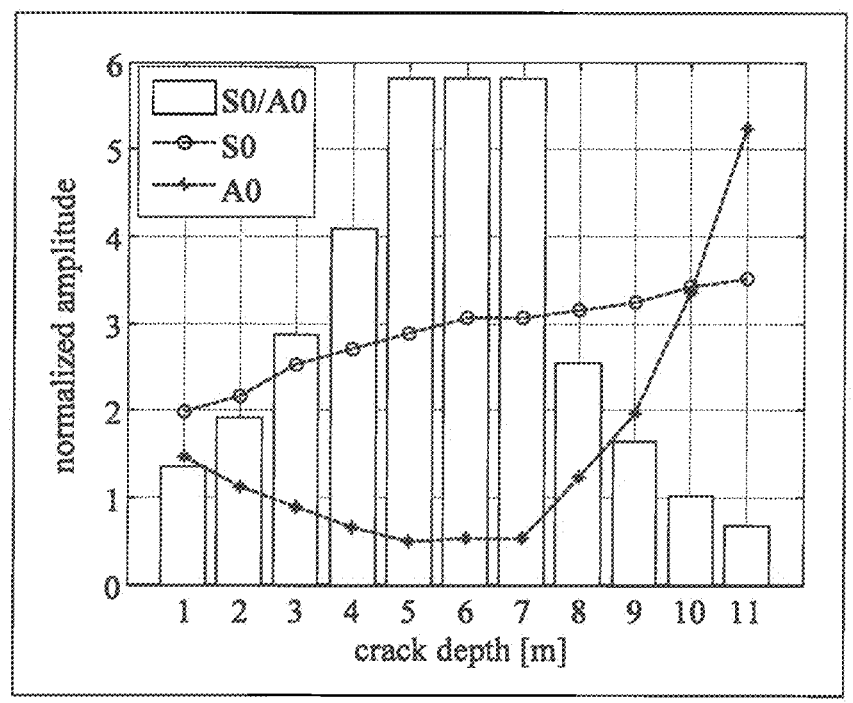

FIG. 5B, for example, illustrates a characteristic curve obtained by such analysis for a structural component of interest. In generating the curve, a 2D plane-strain model of a waveguide was used with a notch being representative for a fatigue crack, as shown in FIG. 5A. In the model the notch is representative for a fatigue crack was constructed using higher-order finite element method (SEM). The acoustic energy was modeled as a disturbance source generating internal stress in the lengthwise direction at the deepest point of the crack.

Based on the 2D model, analysis was performed for a number of AE source depth values in a 12 mm steel plate using the finite element method (FEM). The acoustic energy released by the crack is modeled with a disturbance source generating internal stress at the deepest point of the crack in the considered plane. The symmetric and anti symmetric waves are obtained at point P1 and P2 on the free surfaces of the specimen. To avoid inaccuracies introduced by dispersion of guided waves, either these points should be close to the source, or a dispersion correction should be applied to the received signals. Accordingly, a characteristic curve can be generated that relates crack depth to an amplitude and ratio of wave mode compositions, in particular the S0 and A0 modes.

Since the AE signals are released from the points on the leading edges of the crack, see view B-B in FIG. 3, an estimate of the crack size and depth can be collected. If the characteristic curve in FIG. 5B is used, a unique estimation can be made if at least two S0-to-A0 values for an identified crack point are available. Otherwise, more than one possibility for the crack depth may exist for a certain S0-to-A0 ratio.

For deep cracks, i.e. having a crack depth approaching plate thickness, ratio will be similar to shallow cracks, thus introducing an ambiguity in the characteristic curve. To resolve the ambiguity a history bank is populated with crack depth history, so that for a designated crack, identified by a calculated location of the AE source, its deepness be resolved by matching a calculated ratio with a progress in time of the specific ratio, so that a crack depth can be derived from a position in progress on the characteristic curve.

Figure 6A:
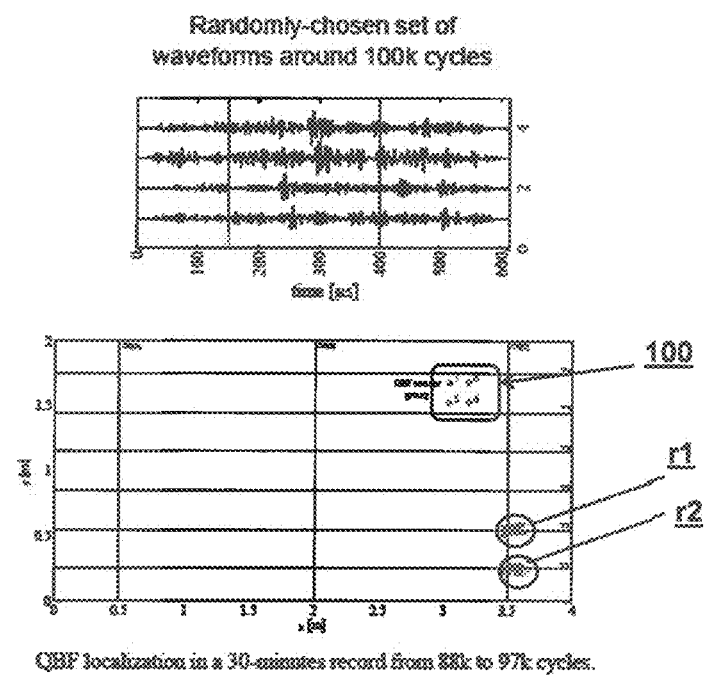
FIGS. 6A and 6B give a further illustration of calculating a minor error.
Figure 6B:
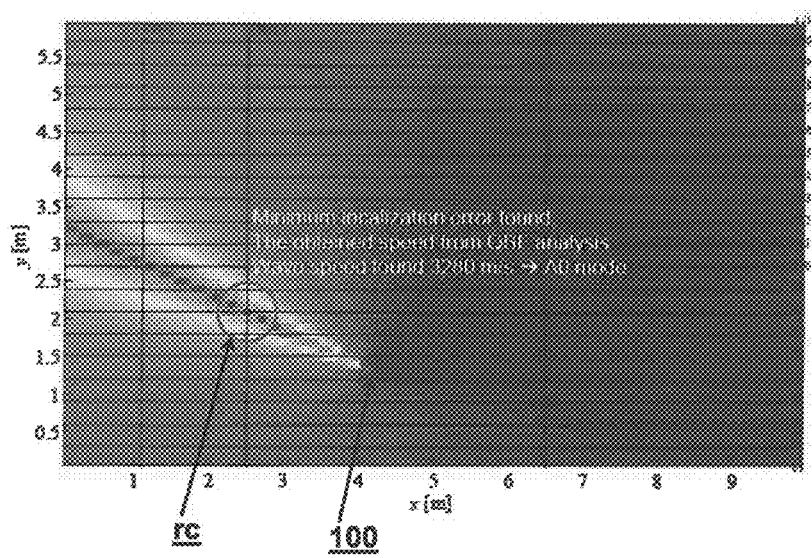

FIGS. 6A and 6B give a further illustration of calculating a minimum error of an error function associated with an assumed combination of the source location, speed of a dominant wave mode, and identified arrival times of dominant and non-dominant wave modes. In FIG. 6A a number of cycles are from time traces of a randomly—chosen set of waveforms of around 100 k cycles resulting in two localized cracks r1 having a depth of 2.9 and length of 32 mm and r2 having a depth of 1 mm and length of 27 mm respectively. The waveforms are recorded by the detectors located on a single device 100 having known relative detector positions, thereby finding a location of sources of acoustic emission on the structure of interest. The area rc indicates a minimum localization error, in a field test wherein the obtained speed from the QBF analysis yielded a wave speed of 3280 m/s of the A0 mode.

Finally, the above-discussion is intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the scope of the present systems and methods as set forth in the claims that follow. The specification and drawings are accordingly to be regarded in an illustrative manner and are not intended to limit the scope of the appended claims. For example, depending on the structure, for example, non-plate structures such as pipes structures or other geometries, corresponding boundary conditions will apply in the Final Element Analysis, which will result in modified dispersion curves and different relations between the guided wave modes and crack depth. For each structure, a sensor arrangement is provided that is able to identify by placing a plurality of AE detectors on the structure of interest with relatively small distances from each other, whether on a square pattern, on a circular pattern, or with other relative locations. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage and are deemed explicitly disclosed by the subject application.

The invention claimed is:

1. A method for crack monitoring in a structure of interest using Acoustic Emission (AE) sensing, comprising:
   placing a plurality of AE detectors on the structure of interest, having relative known positions;
   detecting during a pre-set time window acoustic power emitted by an AE source in the selected detectors as time traces;
   detecting relative time differences of arrival times of a wave mode with maximum acoustic amplitude as dominant wave mode in the time traces of said selected detectors;
   identifying, in a frequency interval of interest a next to maximum acoustic amplitude as a non-dominant wave mode in the time window;
   correlating a ratio of dominant and non-dominant wave mode amplitudes to a crack depth location using a characteristic curve;
   populating in a history bank crack depths measured for corresponding locations, so that for a selected crack, identified by a calculated location of the AE source, its deepness be resolved by matching a calculated ratio of wave mode amplitudes with a progress in time of the specific ratio position in progress on the characteristic curve; and calculating a minimum error of an error function associated with an assumed combination of the source location, speed of a dominant wave mode, and identified arrival times of dominant and non-dominant wave modes, from time traces recorded by said selected detectors located on a single device having known relative detector positions, thereby finding a location of a source of acoustic emission on the structure of interest.

2. The method according to claim 1 wherein the time window of interest for the non-dominant wave mode is chosen based on an identified arrival time of the dominant wave mode; an identified distance from selected detectors to a calculated crack location (xc,yc) and a calculated group speed of the dominant and non-dominant wave modes.

3. The method according to claim 1 further comprising,
correcting for dispersion based on the model, to reconstruct an original ratio of wave modes at the source of emission, and
correlating the original ratio of wave modes to a crack depth.

4. A method according to claim 1, wherein a threshold criterion starts the time window for detecting the time traces.

5. A method according to claim 1, wherein the error function is a quadratic optimization function.

6. A method according to claim 1, wherein the structure of interest is metallic and thin-walled, and the wave modes are expressed as zero order guides waves S0 and A0.

7. A system for crack monitoring in a structure of interest using Acoustic Emission (AE) sensing, the system comprising:
a computer;
a plurality of AE detectors; and
a history bank,
wherein, the computer is programmed to:
detect relative time differences of arrival times of a wave mode with maximum acoustic amplitude as dominant wave mode in time traces of selected AE detectors to be placed on the structure of interest arranged for detecting during a pre-set time window acoustic power emitted by an AE source, the detectors having relative known positions;

identify, in a frequency interval of interest, a next to maximum acoustic amplitude as a non-dominant wave mode in the time window;

correlate a ratio of dominant and non-dominant wave mode amplitudes to a crack depth location using a characteristic curve;

populate in the history bank crack depths measured for corresponding locations, so that for a selected crack identified by a calculated location of the AE source, its depth is resolved by matching a calculated ratio of wave mode amplitudes with a progress in time of the specific ratio position in progress on the characteristic curve; and calculate a minimum error of an error function associated with an assumed combination of the source location, speed of a dominant wave mode, and identified arrival times of dominant and non-dominant wave modes, from time traces recorded by said selected detectors located on a single device having known relative detector positions, thereby finding a location of a source of acoustic emission on the structure of interest.

8. Non-transient computer-readable storage medium with program instructions that, when run on a system for crack monitoring in a structure of interest, comprising means for extracting wave modes existing in a frequency interval of interest, means for finding a source of emission on the structure of interest, means for correcting for dispersion to reconstruct an original ratio of wave modes at the source of emission, and means for correlating the original ratio of wave modes to a crack depth, said means combined on a single device and said device further comprising a plurality of AE detectors having relative known positions that can be placed on the structure of interest, cause the system to perform the method of claim 1.

* * * * *